(12) United States Patent
Bogaert et al.

(10) Patent No.: US 9,987,127 B2
(45) Date of Patent: Jun. 5, 2018

(54) TORIC LENS WITH DECREASED SENSITIVITY TO CYLINDER POWER AND ROTATION AND METHOD OF USING THE SAME

(71) Applicant: AMO GRONINGEN B.V., Groningen (NL)

(72) Inventors: Theophilus Bogaert, Groningen (NL); Hendrik A. Weeber, Groningen (NL); Huawei Zhao, Irvine, CA (US)

(73) Assignee: AMO Groningen B.V., Groningen (NL)

( * ) Notice: Subject to any disclaimer, the term of this patent is extended or adjusted under 35 U.S.C. 154(b) by 0 days. days.

(21) Appl. No.: 14/975,364

(22) Filed: Dec. 18, 2015

(65) Prior Publication Data

US 2016/0100938 A1   Apr. 14, 2016

Related U.S. Application Data

(60) Division of application No. 12/832,816, filed on Jul. 8, 2010, now Pat. No. 9,216,080, which is a
(Continued)

(51) Int. Cl.
*A61F 2/16* (2006.01)
*G02B 3/06* (2006.01)
(Continued)

(52) U.S. Cl.
CPC .......... *A61F 2/1654* (2013.01); *A61B 3/0025* (2013.01); *A61F 2/1645* (2015.04);
(Continued)

(58) Field of Classification Search
CPC . A61F 2/1618; A61F 2/1654; G02C 2202/20; G02C 7/06; G02C 7/042
See application file for complete search history.

(56) References Cited

U.S. PATENT DOCUMENTS 2,077,092 A   4/1937   Broder
3,305,294 A   2/1967   Alvarez
(Continued)

FOREIGN PATENT DOCUMENTS

CA   2722274 A1   10/2009
CN   1035363 A    9/1989
(Continued)

OTHER PUBLICATIONS

Alfonso J.F., et al., "Prospective Study of the Acri.LISA Bifocal Intraocular Lens," Journal of Cataract Refractive Surgery, 2007, vol. 33 (11), pp. 1930-1935.
(Continued)

*Primary Examiner* — David H Willse
*Assistant Examiner* — Tiffany Shipmon
(74) *Attorney, Agent, or Firm* — Johnson & Johnson Surgical Vision, Inc.

(57) ABSTRACT

A method, system and apparatus for vision correction are disclosed. The method, system and apparatus include a toric intraocular element for correcting astigmatism and having a cylinder power, and a depth of focus extender coupled to the toric intraocular element, the depth of focus extender extending a depth of focus. The extended depth of focus may reduce sensitivity of the toric intraocular element to at least one of rotation and selected cylinder power.

6 Claims, 8 Drawing Sheets

Related U.S. Application Data continuation-in-part of application No. 12/120,201, filed on May 13, 2008, now Pat. No. 8,740,978, which is a continuation-in-part of application No. 12/197,249, filed on Aug. 23, 2008, now Pat. No. 8,747,466.

(60) Provisional application No. 60/968,250, filed on Aug. 27, 2007.

(51) Int. Cl.

| | | |
|---|---|---|
| *G02B 27/00* | (2006.01) | |
| *G02C 7/02* | (2006.01) | |
| *G02C 7/04* | (2006.01) | |
| *A61B 3/00* | (2006.01) | |
| *A61F 9/013* | (2006.01) | |
| *G02C 7/06* | (2006.01) | |

(52) U.S. Cl.
CPC ............... *A61F 9/013* (2013.01); *G02B 3/06* (2013.01); *G02B 27/0075* (2013.01); *G02C 7/02* (2013.01); *G02C 7/027* (2013.01); *G02C 7/041* (2013.01); *G02C 7/06* (2013.01); *A61F 2002/1699* (2015.04); *G02C 2202/02* (2013.01); *G02C 2202/06* (2013.01); *G02C 2202/20* (2013.01)

(56) References Cited

U.S. PATENT DOCUMENTS

| | | |
|---|---|---|
| 3,367,734 A | 2/1968 | Karl et al. |
| 3,735,685 A | 5/1973 | Plummer |
| 4,010,496 A | 3/1977 | Neefe |
| 4,077,071 A | 3/1978 | Freeman |
| 4,093,361 A | 6/1978 | Erickson et al. |
| 4,134,160 A | 1/1979 | Bayers |
| 4,162,122 A | 7/1979 | Cohen |
| 4,174,543 A | 11/1979 | Kelman |
| 4,210,391 A | 7/1980 | Cohen |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,593,981 A | 6/1986 | Scilipoti |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,636,049 A | 1/1987 | Blaker |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | LeMaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee et al. |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,225,858 A | 7/1993 | Portney |
| 5,225,997 A | 7/1993 | Lederer et al. |
| 5,229,797 A | 7/1993 | Futhey et al. |
| 5,258,025 A | 11/1993 | Fedorov et al. |
| 5,278,592 A | 1/1994 | Marie et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,652,638 A | 7/1997 | Roffman et al. |
| 5,691,800 A | 11/1997 | Iki et al. |
| 5,699,142 A | 12/1997 | Lee et al. |
| 5,715,031 A | 2/1998 | Roffman et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 6,015,435 A | 1/2000 | Valunin et al. |
| 6,051,024 A | 4/2000 | Cumming |
| 6,055,111 A | 4/2000 | Nomura et al. |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |
| 6,179,870 B1 | 1/2001 | Sourdille et al. |
| 6,210,005 B1 | 4/2001 | Portney |
| 6,235,055 B1 | 5/2001 | Chu |
| 6,261,321 B1 | 7/2001 | Kellan |
| 6,319,282 B1 | 11/2001 | Nishi |
| 6,338,559 B1 | 1/2002 | Williams et al. |

(56) References Cited

U.S. PATENT DOCUMENTS

| | | |
|---|---|---|
| 6,419,697 B1 | 7/2002 | Kelman |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,709,102 B2 | 3/2004 | Duppstadt |
| 6,802,605 B2 | 10/2004 | Cox et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,993,398 B2 | 8/2011 | Deacon et al. |
| 8,002,827 B2 | 8/2011 | Deacon et al. |
| 8,018,164 B2 | 9/2011 | Shannon et al. |
| 8,231,219 B2 | 7/2012 | Weeber |
| 8,241,354 B2 | 8/2012 | Hong et al. |
| 8,382,281 B2 | 2/2013 | Weeber |
| 8,430,508 B2 | 4/2013 | Weeber |
| 8,480,228 B2 | 7/2013 | Weeber |
| 8,573,775 B2 | 11/2013 | Weeber |
| 8,747,466 B2 | 6/2014 | Weeber et al. |
| 8,770,745 B2 | 7/2014 | Lindacher et al. |
| 8,862,447 B2 | 10/2014 | Weeber |
| 2001/0035935 A1 | 11/2001 | Bhalakia et al. |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0054358 A1 | 3/2004 | Cox et al. |
| 2004/0068317 A1 | 4/2004 | Knight |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150790 A1 | 8/2004 | Roffman et al. |
| 2004/0156014 A1 | 8/2004 | Piers et al. |
| 2004/0167622 A1 | 8/2004 | Sunalp et al. |
| 2005/0096226 A1 | 5/2005 | Stock et al. |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0066808 A1 | 3/2006 | Blum et al. |
| 2006/0068453 A1 | 3/2006 | Altieri |
| 2006/0098162 A1* | 5/2006 | Bandhauer ............ A61F 2/1618 351/159.44 |
| 2006/0109421 A1 | 5/2006 | Ye et al. |
| 2006/0116763 A1 | 6/2006 | Simpson |
| 2006/0116764 A1* | 6/2006 | Simpson ................ A61F 2/164 351/159.11 |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161914 A1 | 7/2008 | Brady et al. |
| 2008/0231809 A1 | 9/2008 | Haigis |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0210054 A1 | 8/2009 | Weeber et al. |
| 2009/0234448 A1 | 9/2009 | Weeber et al. |
| 2009/0279048 A1 | 11/2009 | Hong et al. |
| 2009/0323020 A1 | 12/2009 | Zhao et al. |
| 2010/0016965 A1 | 1/2010 | Hong et al. |
| 2010/0082017 A1 | 4/2010 | Zickler et al. |
| 2010/0100178 A1 | 4/2010 | Weeber et al. |
| 2010/0161048 A1 | 6/2010 | Schaper, Jr. |
| 2010/0274234 A1 | 10/2010 | Liang |
| 2012/0140166 A1 | 6/2012 | Zhao |
| 2012/0320334 A1 | 12/2012 | Ho et al. |

FOREIGN PATENT DOCUMENTS

| | | |
|---|---|---|
| CN | 1039487 A | 2/1990 |
| CN | 1406120 A | 3/2003 |
| CN | 1833192 A | 9/2006 |
| DE | 8107675 U1 | 7/1981 |
| EP | 226400 A2 | 6/1987 |
| EP | 227357 A2 | 7/1987 |
| EP | 0343067 A1 | 11/1989 |
| EP | 0457553 A2 | 11/1991 |
| EP | 681198 A1 | 11/1995 |
| EP | 0926531 A1 | 6/1999 |
| EP | 949529 A2 | 10/1999 |
| EP | 957331 A2 | 11/1999 |
| EP | 1310267 B1 | 1/2008 |
| EP | 1424049 B1 | 6/2009 |
| EP | 2182891 B1 | 4/2014 |
| FR | 2745711 A1 | 9/1997 |
| JP | H0255314 A | 2/1990 |
| WO | 8603961 A1 | 7/1986 |
| WO | 9222264 A1 | 12/1992 |
| WO | 9303409 A1 | 2/1993 |
| WO | 9507487 A1 | 3/1995 |
| WO | 9855315 A1 | 12/1998 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |

(56) References Cited

FOREIGN PATENT DOCUMENTS

| WO | 0182839 A1 | 11/2001 |
|---|---|---|
| WO | 0189424 A1 | 11/2001 |
| WO | 0221194 A2 | 3/2002 |
| WO | 03009053 A1 | 1/2003 |
| WO | 2004034129 A1 | 4/2004 |
| WO | 2004090611 A2 | 10/2004 |
| WO | 2004096014 A2 | 11/2004 |
| WO | 2005019906 A1 | 3/2005 |
| WO | 2006025726 A1 | 3/2006 |
| WO | 2006032263 A2 | 3/2006 |
| WO | 2006047698 A1 | 5/2006 |
| WO | 2006060477 A2 | 6/2006 |
| WO | 2006060480 A2 | 6/2006 |
| WO | 2007067872 A2 | 6/2007 |
| WO | 2007092948 A1 | 8/2007 |
| WO | 2007133384 A2 | 11/2007 |
| WO | 2008045847 A2 | 4/2008 |
| WO | 2008083283 A2 | 7/2008 |
| WO | 2009020963 A1 | 2/2009 |
| WO | 2009029515 A1 | 3/2009 |
| WO | 2009058755 A1 | 5/2009 |
| WO | 2009076670 A1 | 6/2009 |
| WO | 2009137491 A1 | 11/2009 |
| WO | 2010009254 A1 | 1/2010 |
| WO | 2010009257 A1 | 1/2010 |

OTHER PUBLICATIONS

Alio J.L., et al., "Phakic Anterior Chamber Lenses for the Correction of Myopia: A 7-Year Cumulative Analysis of Complications in 263 Cases," Ophthalmology, 1999, vol. 106 (3), pp. 458-466.

Apple D.J., et al., "Anterior Chamber Lenses Part 1: Complications and Pathology and a Review of Designs," Journal of Cataract Refractive Surgery, 1987, vol. 13 (2), pp. 157-174.

Apple D.J., et al., Eds., "Intraocular Lenses: Evolution, Designs, Complications and Pathology," in: New Concepts in Intraocular Lens Implantation, Williams & Wilkins publisher, 1989, vol. 36 (1), pp. 21-36.

Apple D.J., et al., Eds., "Intraocular Lenses: Evolution, Designs, Complications and Pathology," in: New Concepts in Intraocular Lens Implantation, Williams & Wilkins publisher, 1989, vol. 22 (36), pp. 205-221.

Baikoff G., et al., "Angle-fixated Anterior Chamber Phakic Intraocular Lens for Myopia 7 to -19 Diopters," Journal of Refractive Surgery, 1998, vol. 14 (3), pp. 282-292.

Canovas C., et al., "Hybrid Adaptive-Optics Visual Simulator," Optical Letters, 2010, vol. 35 (2), pp. 196-198.

Cheng X., et al., "Predicting Subjective Judgment of Best Focus with Objective Image Quality Metrics," Journal of Vision, 2004, vol. 4 (4), pp. 310-321.

CILCO Advertisement Brochure, Oct. 1982, 3 pages.

Cohen A.L., "Practical Design of a Bifocal Hologram Contact Lens or Intraocular Lens," Applied Optics, 1992, vol. 31 (19), pp. 3750-3754.

De Almeida M.S., et al., "Different Schematic Eyes and their Accuracy to the in Vivo Eye: A Quantitative Comparison Study," Brazilian Journal of Physics, 2007, vol. 37 (2A), 10 pages.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, 1992, vol. 1780, pp. 393-402.

Kim J.H., et al., "The Analysis of Predicted Capsular Bag Diameter using Modified Model of Capsule Measuring Ring in Asians," Clinical and Experimental Ophthalmology, 2008, vol. 36 (3), pp. 238-244.

Liou H.L., et al., "Anatomically Accurate, Finite Model Eye for Optical Modeling," Journal of Optical Society of America, 1997, vol. 14 (8), pp. 1684-1695.

Liou H.L., et al., "The Prediction of Spherical Aberration with Schematic Eyes," Ophthalmic and Physiological Optics, 1996, vol. 16 (4), pp. 348-354.

Marinho A., "Results are Encouraging for Phakic IOLs, but More Work is needed," Refractive Surgery, 2000, p. 12, 15.

Marsack J.D., et al., "Metrics of Optical Quality Derived from Wave Aberrations Predict Visual Performance," Journal of Vision, 2004, vol. 4 (4), pp. 322-328.

Menapace R., "The Capsular Tension Rings," Journal of Cataract & Refractive Surgery, 2008, Chap. 3, pp. 27-44.

Monsoriu J.A., et al., "Devil's Lenses," Optics Express, 2007, vol. 15 (21), pp. 13858-13864.

Navarro R., et al., "Accommodation-Dependent Model of the Human Eye with Aspherics," Journal of the Optical Society of America, 1985, vol. 2 (8), pp. 1273-1281.

Nio Y.K., et al., "Effect of Intraocular Lens Implantation on Visual Acuity, Contrast Sensitivity, and Depth of Focus," Journal of Cataract and Refractive Surgery, 2003, vol. 29 (11), pp. 2073-2081.

Norrby S., et al., "Model Eyes for Evaluation of Intraocular Lenses," Applied Optics, 2007, vol. 46 (26), pp. 6595-6605.

Olsen T., "Simple Method to Calculate the Surgically Induced Refractive Change," Journal of Cataract & Refractive Surgery, 1993, vol. 19 (2), pp. 319-320.

Piers P.A., et al., "Eye Models for the Prediction of Contrast Vision in Patients with New Intraocular Lens Designs," Optics Letters, 2004, vol. 29 (7), pp. 733-735.

Piers P.A., et al., "Theoretical Comparison of Aberration-Correcting Customized and Aspheric Intraocular Lenses," Journal of Refractive Surgery, 2007, vol. 23 (4), pp. 374-384.

Praeger D.L., "Praeger Technique for the Insertion of the Copeland Radial IOL Posterior Chamber Placement," Copeland Lens, 1982, 7 pages.

Siedlecki D., et al., "Radial Gradient index Intraocular Lens: a Theoretical Model," Journal of Modern Optics, 2008, vol. 55 (4-5), pp. 639-647.

Strenn K., et al., "Capsular bag Shrinkage after Implantation of an Open-Loop Silicone Lens and a Poly(methyl methacrylate) Capsule Tension Ring," Journal of Cataract and Refractive Surgery, 1997, vol. 23 (10), pp. 1543-1547.

Tehrani M., et al., "Capsule Measuring Ring to Predict Capsular Bag Diameter and Follow its Course after Foldable Intraocular Lens Implantation," Journal of Cataract Refractive Surgery, 2003, vol. 29 (11), pp. 2127-2134.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.

Van Den Berg T.J., "Analysis of Intraocular Straylight, Especially in Relation to Age," Optometry and Vision Science, 1995, vol. 72 (2), pp. 52-59.

Van Meeteren A., "Calculations on the Optical Modulation Transfer Function of the Human Eye for White Light," Optica Acta, 1974, vol. 21 (5), pp. 395-412.

Vass C., et al., "Prediction of Pseudophakic Capsular bag Diameter based on Biometric Variables," Journal of Cataract and Refractive Surgery, 1999, vol. 25 (10), pp. 1376-1381.

Villegas E.A., et al., "Correlation between Optical and Psychophy, Sical Parameters as a Function of Defocus," Optometry and Vision Science, 2002, vol. 79 (1), pp. 60-67.

European Search Report for Application No. EP11165087, dated Jul. 22, 2011, 6 pages.

European Search Report for Application No. EP89304883, dated Sep. 3, 1990, 1 page.

\* cited by examiner

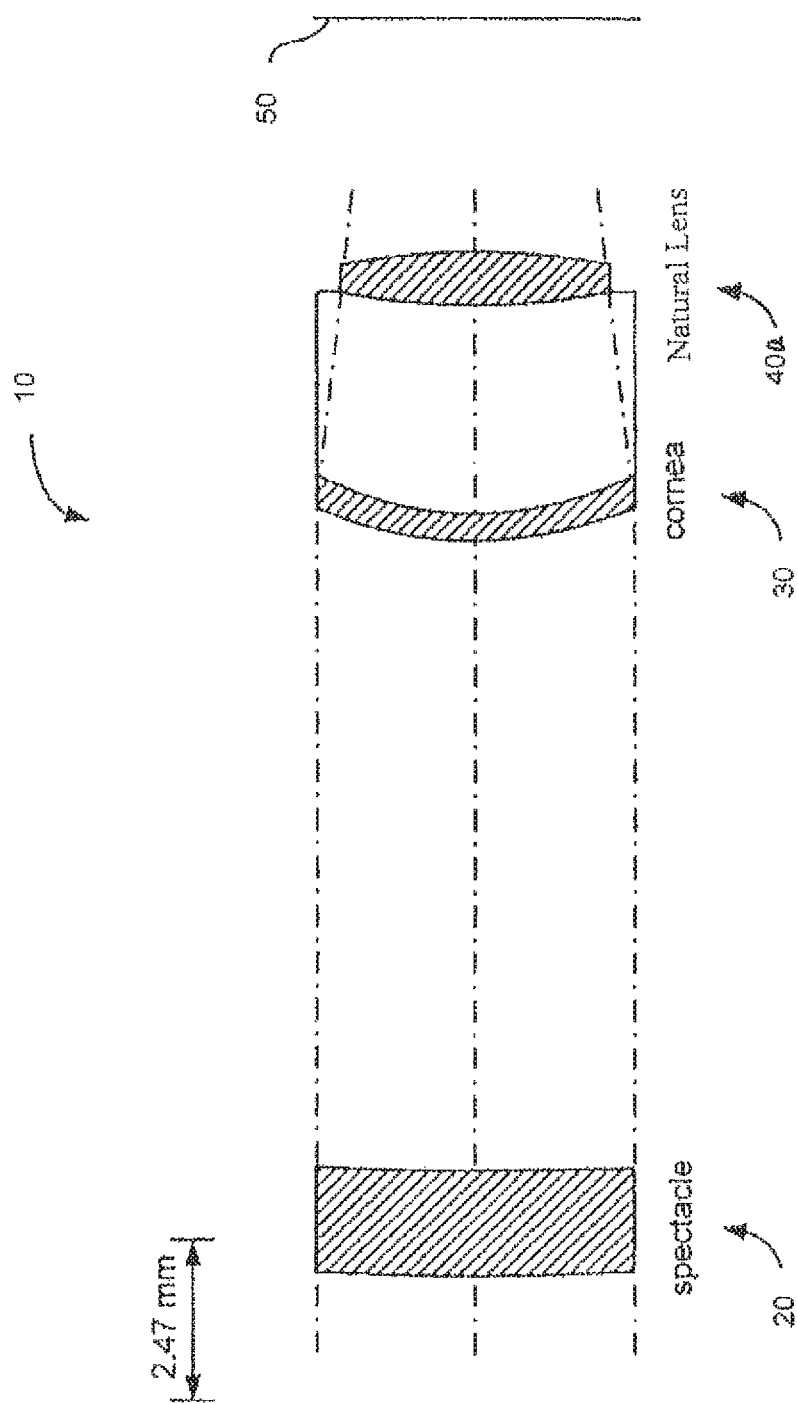

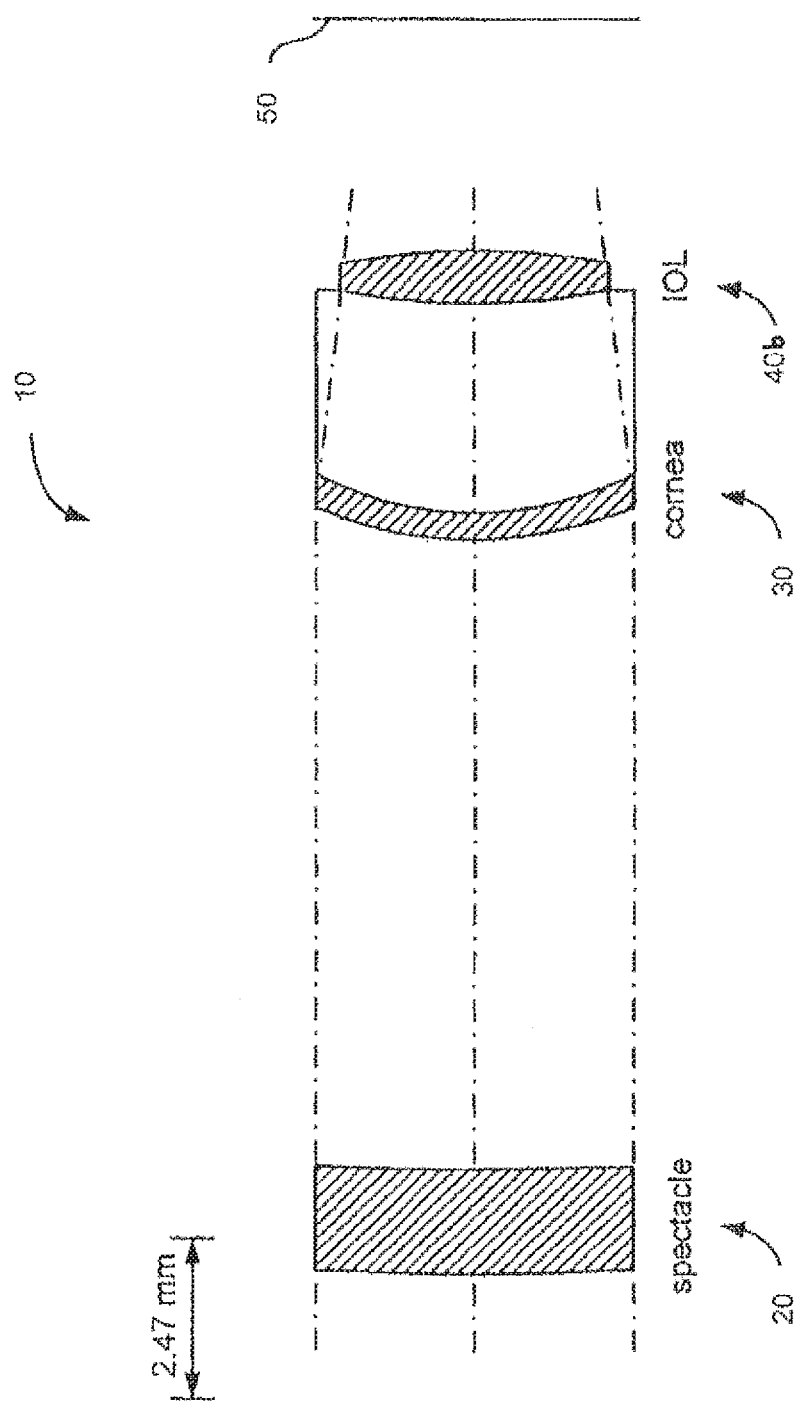

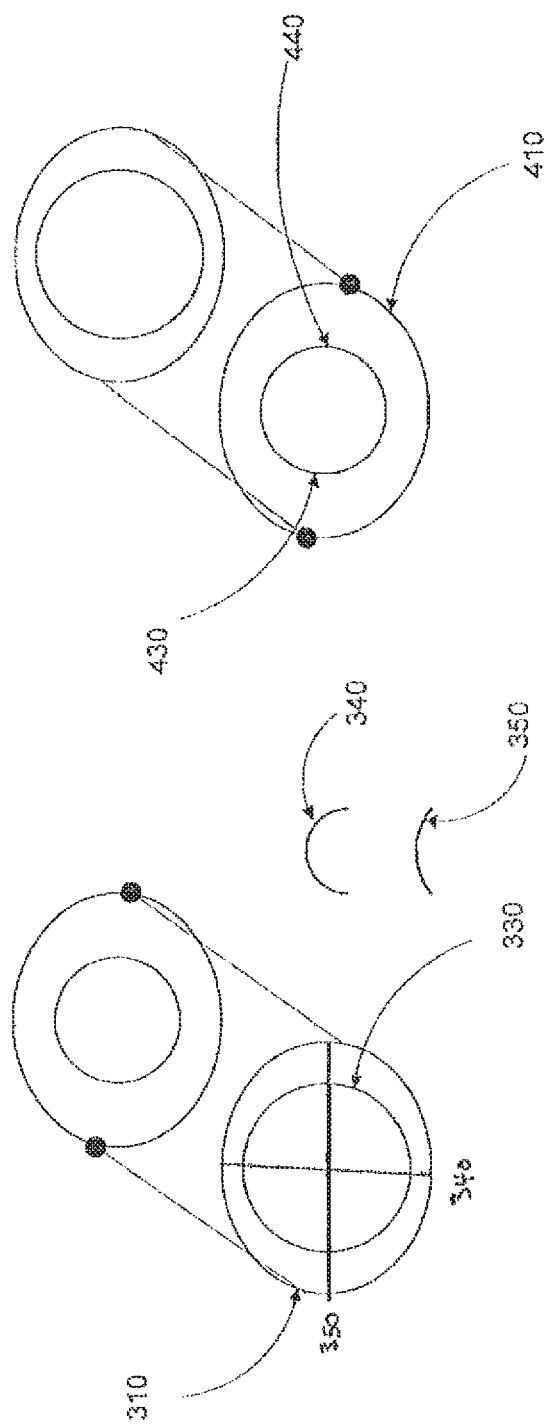

TORIC LENS WITH DECREASED SENSITIVITY TO CYLINDER POWER AND ROTATION AND METHOD OF USING THE SAME

CROSS-REFERENCE OF RELATED APPLICATIONS

This application claims priority to and is a divisional application of U.S. application Ser. No. 12/832,816 filed on Jul. 8, 2010, which claims priority to and is a continuation-in-part application of both U.S. application Ser. No. 12/120,201, filed on May 13, 2008 and U.S. application Ser. No. 12/197,249, filed on Aug. 23, 2008, both of which claim priority to U.S. Provisional Application No. 60/968,250, filed on Aug. 27, 2007. The aforementioned applications are hereby incorporated by reference as if set forth herein in their entirety.

FIELD OF THE INVENTION

The present invention is related to vision correction, and, more particularly, to vision correction using a toric lens with decreased sensitivity to cylinder power and rotation.

BACKGROUND OF THE INVENTION

Surgery on the human eye has become commonplace in recent years. Many patients pursue eye surgery as an elective procedure, such as to avoid the use of contacts or glasses, and other patients may find it necessary to pursue surgery to correct an adverse condition in the eye. Such adverse conditions may include, for example, cataracts or presbyopia, as well as other conditions known to those skilled in the art that may negatively affect elements of the eye.

The anatomy and physiology of the human eye is well understood. Generally speaking, the structure of the human eye includes an outer portion, also referred to as a layer, formed of two parts, namely the cornea and the sclera. The middle layer of the eye includes the iris, the choroid, and the ciliary body. The inner layer of the eye includes the retina. The eye also includes, physically associated with the middle layer, a crystalline lens that is contained within an elastic capsule, referred to herein as the lens capsule, or capsular bag.

Image formation in the eye occurs by entry of image-forming light to the eye through the cornea, and refraction by the cornea and the crystalline lens to focus the image-forming light on the retina. The retina provides the light sensitive tissue of the eye.

Functionally, the cornea has a greater, and generally constant, optical power in comparison to the crystalline lens. The power of the crystalline lens, while smaller than that of the cornea, may be changed when the eye needs to focus at different distances. This change, or "accommodation," is achieved by changing the shape of the crystalline lens. Accommodation, as used herein, includes the making of a change in the focus of the eye for different distances. For example, in order to change the shape of the crystalline lens for accommodation, the ciliary muscles may contract to cause ligaments that support the crystalline lens to relax, thereby allowing the crystalline lens to become more rounded.

The iris operates to change the aperture size of the eye. More specifically, the diameter of the incoming light beam is controlled by the iris, which provides the aperture of the eye, and the ciliary muscles may contract, as referenced above, to provide accommodation in conjunction with any needed change in the size of the aperture provided by the iris. The opening, or aperture, in the iris is called the pupil.

Correction of defects or degradation in the aspects of the eye may occur surgically, as mentioned above. In a simple example, it is common to wear glasses or contact lenses to improve vision by correcting myopic (near-sighted), hyperopic (far-sighted) and astigmatic eyesight. Rather than relying on glasses or contacts, elective laser refractive surgery, or other eye surgery, may serve to improve the refractive state of the eye, including improvement to astigmatism, and may thereby decrease or eliminate dependency on glasses or contact lenses. Such surgeries may include various methods of surgical remodeling of the cornea, or cataract surgery, for example. Surgery may also serve to implant an intraocular lens (IOL), either in addition to the crystalline lens, which addition is referred to as a phakic IOL, or upon removal of the crystalline lens, which replacement is referred to as a pseudophakic IOL.

In particular, an IOL may be a lens implanted in the eye, such as to replace the existing crystalline lens when the crystalline lens has been clouded over by a cataract, for example, or as a refractive element to change the eye's optical power. An IOL is one type of corrective lens that may change the focus of the elements of the eye. This change in focus provided by a corrective lens is herein referred to as defocus.

An IOL may consist of a small plastic lens with plastic side struts, called haptics, to hold the lens in place within the capsular bag. An IOL may be made of a relatively inflexible material, such as polymethyl methacrylate (PMMA), for example, or of a flexible material, such as silicone, acrylic, hydrogels, and the like. An IOL may be a fixed monofocal lens matched to distance vision, for example. An IOL may also be multifocal to provide the recipient with multiple-focused vision at far and reading distances, for example. An IOL may be used to provide the patient with limited visual accommodation, for example.

An IOL may be either spheric or toric. Spheric IOLs are used for correction of a myriad of vision problems, while toric IOLs are typically used for astigmatic eye correction. When using a toric IOL, the angular orientation of the IOL in the eye is particularly important, as a toric IOL is intended for positioning after insertion at a specific angle, and, in currently available methods, that insertion angle must be maintained, post-insertion, in order to provide a proper astigmatic correction. If the insertion angle is not correct and/or maintained, the astigmatism will not be fully corrected, and in fact the astigmatic condition may worsen. The condition caused by this misalignment of the IOL is often referred to as residual cylinder, or remaining astigmatism.

Generally, astigmatism is an optical defect in which vision is blurred due to the ocular inability to focus a point object into a sharply focused image on the retina. This may be due to an irregular, or toric, curvature of the cornea and/or lens. The refractive error of the astigmatic eye stems from a difference in degree of curvature, and therefore in degree of refraction, of the different meridians of the cornea and/or the crystalline lens, which causes the eye to have two focal points, one correspondent to each meridian. As used herein, a meridian includes one of two axes that subtend a curved surface, such as the prime meridian on the earth, for example. Meridians may be orthogonal. By way of example, the meridians of the earth may be any orthogonal line of longitude and any line of latitude that curve about the surface of the earth.

For example, in an astigmatic eye, an image may be clearly focused on the retina in the horizontal (sagittal) plane, but may be focused behind the retina in the vertical (tangential) plane. In the case where the astigmatism results only from the cornea, the two astigmatism meridians may be the two axes of the cornea. If the astigmatism results from the crystalline lens, the two astigmatism meridians may be the two axes of the crystalline lens. If the astigmatism results from a combination of the cornea and the crystalline lens, the two astigmatism meridians may be the respective axes of the combined lenses of the cornea and the crystalline lens.

Astigmatism arising from the cornea or crystalline lens, or the combination of the two lenses, may be corrected by a toric lens, such as the aforementioned toric IOL. A toric surface resembles a section of the surface of a football, for which there are two regular radii of curvature, one smaller than another. These radii may be used to correct the defocus in the two meridians of the astigmatic eye. Thus, blurred vision caused by astigmatism may be corrected by corrective lenses or laser vision correction, such as glasses, hard contact lenses, contact lenses, and/or an IOL, that provide a compensating optic specifically rotated around the optical axis. However, any misalignment of the compensating optic, and/or improper selection of the corrective lens, may cause residual cylinder, or further astigmatism, and potentially induce other aberrations. The aberrations may be exacerbated if, for example multifocal and toric corrective lenses are required to correct the initial condition, and the respective corrective lenses are misaligned. Similarly, an initial condition may be exacerbated with misalignment of aspheric surfaces used to correct spherical aberration, for example.

Thus, two specific issues arise from using a lens, such as an IOL, to correct astigmatism. First, toric ophthalmic lenses are sensitive to cylinder orientation misalignment relative to that to be corrected, such as wherein the axis of the toric lens in the eye and the lens for correction are not accurately aligned. Second, the cylinder power of the eye or cornea may not sufficiently match the power of the toric IOL. This may be due to measurement errors, unintended changes of cylinder power and/or axis during or after surgery, or because current toric lenses are offered only in a number of discrete cylinder increments.

A need therefore exists for a lens, such as an IOL, having decreased sensitivity to alignment errors and also having decreased sensitivity to selection of the proper cylinder power, and for an optical system and method of providing and using the same.

SUMMARY OF THE INVENTION

The present invention is and includes apparatuses, systems, and methods for vision correction. An intraocular lens and a vision corrective system as provided in the present invention may include a toric intraocular element for correcting astigmatism and having a cylinder power, and a depth of focus extender coupled to the toric intraocular element, the depth of focus extender extending a depth of focus. The extended depth of focus may reduce sensitivity of the toric intraocular element to at least one of rotation and selected cylinder power.

A vision corrective optic and optical system as provided in the present invention may include a lens for correcting at least one aspect of an eye, the at least one aspect including at least one aberration, and a depth of focus extender coupled with the lens, the depth of focus extender extending a depth of focus of the lens. The depth of focus extender may increase at least one of alignment tolerance and matching to the at least one aberration.

Also provided is a method for decreasing sensitivity of astigmatic correction to errors of cylinder power selection and lens rotational alignment. The method may include receiving a measure of the astigmatism, receiving a selection of a toric lens matched to a negative of the astigmatism, receiving a determination of a depth of focus extension for coupling with the selected toric lens, coupling the determined depth of focus extension and the selected toric lens, and inserting the coupled depth of focus extension and the selected toric lens in a line of sight.

Therefore, the present invention provides a lens, such as an IOL, having decreased sensitivity to alignment errors and to selection of proper cylinder power, and a system and method of providing and using the same.

BRIEF DESCRIPTION OF THE FIGURES

Understanding of the present invention will be facilitated by consideration of the following detailed description of the preferred embodiments of the present invention taken in conjunction with the accompanying drawings, in which like numerals refer to like parts, and in which:

FIG. 1A is a schematic diagram of the optics of an eye;

FIG. 1B is a schematic diagram of the optics of an eye;

FIG. 4 is a depiction of the anterior surface of a lens according to an aspect of the present invention;

FIG. 5 is a depiction of the posterior surface of a lens according to an aspect of the present invention;

DETAILED DESCRIPTION OF THE PREFERRED EMBODIMENTS

Figure 2:
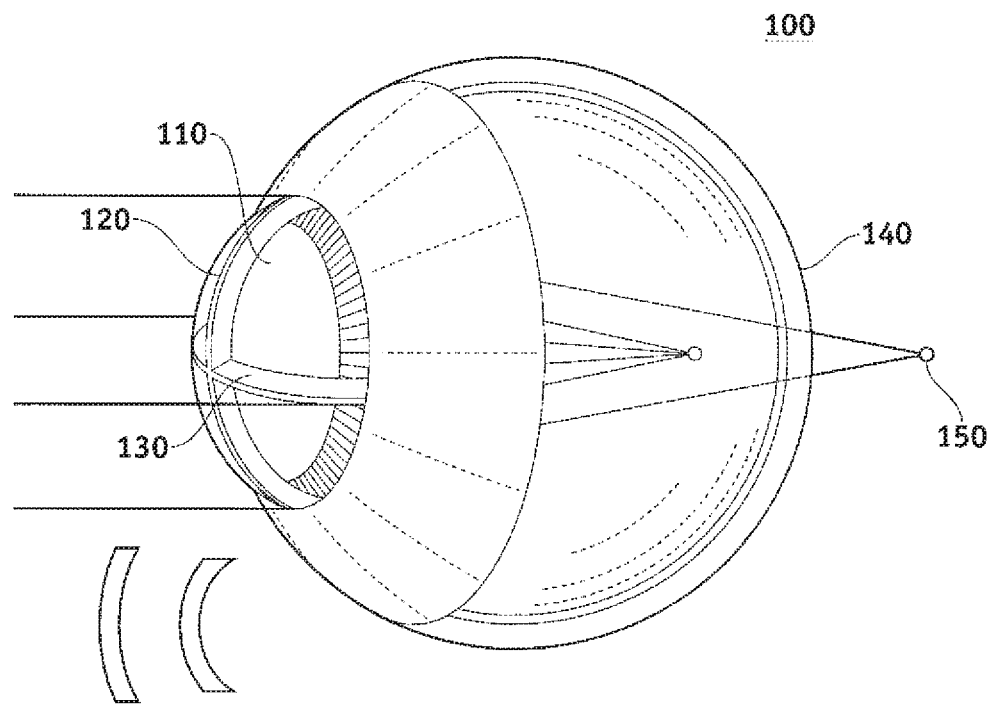
FIG. 2 is a depiction of an eye having astigmatism.

It is to be understood that the figures and descriptions of the present invention have been simplified to illustrate elements that are relevant for a clear understanding of the present invention, while eliminating, for the purpose of clarity, many other elements found in typical lenses, lens systems and methods. Those of ordinary skill in the pertinent arts may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the pertinent arts.

Embodiments described herein provide a corrective lens, such as a toric lens, e.g. a toric IOL, toric contact lens, and/or toric inlay/onlay, having decreased sensitivity to alignment errors and to selection of the proper cylinder power in corrective optics. The described corrective lens, system and method provide an improved vision after implantation, and a decreased dependence on surgical skill. The present embodiments further eliminate dependence of the extent of vision correction on variations in patient healing after surgery, and, as such, greatly improves patient results, and patient comfort, following corrective optic implantation.

The disclosure also includes IOLs, contact lenses, spectacle lenses, and corneal inlays, as well as corneal reshaping procedures and combinations of the foregoing. Embodiments described herein also include a toric lens and an element extending the depth of focus, and may include each in combination with other refractive corrections, such as accommodating ophthalmic corrections, higher order aberration corrections, adjustable refractive corrections, and multifocal refractive corrections, by way of non-limiting example.

According to an embodiment, an exemplary intraocular lens may include a toric intraocular element for correcting astigmatism, and a depth of focus extender coupled to the toric intraocular element, wherein the depth of focus extender extending a depth of focus. As used herein "coupled" and "coupling" is defined to include separate elements and/or integral surfaces, such as in a single lens, for example. The extended depth of focus may reduce sensitivity of the toric intraocular element to at least one of rotation and the selected cylinder power of the toric element.

Referring now to FIG. 1A, illustrated is a schematic diagram of the optical system 10 of an eye. As may be seen in FIG. 1A, optical system 10 may include a spectacle lens 20, a cornea 30, a natural lens 40a, and a retina 50.

Referring now to FIG. 1B, illustrated is a schematic diagram of the optical system 10 of an eye. As may be seen in FIG. 1B, optical system 10 may include a spectacle lens 20, a cornea 30, an intraocular lens 40b, and a retina 50. Of note, intraocular lens 40b in FIG. 1B has replaced natural lens 40a of FIG. 1A in the illustrated embodiment. In the depictions of FIGS. 1A and 1B, cornea 30 may include an aberration, such as the spherical aberration of an average cataract patient as would be understood by those possessing an ordinary skill in the pertinent arts. System 10 may also include a chromatic aberration of the human eye, for example.

By changing the power of the lens 20 the defocus of the eye may be changed. Therefore, the image quality on the retina as a function of the amount of ocular defocus may be determined. This function may be referred to as a defocus curve. Image quality may be defined as a characteristic of an image that measures the perceived image degradation from, typically, an ideal image. Image quality may be measured using a point spread function, defocus curves, a modulation transfer function, or by analysis of the Zernike polynomial, for example, or by using other mathematical modeling or representation techniques. The point spread function represents the intensity distribution of a point source as imaged through the optics of the eye. The strehl ratio is the maximum of the point spread function relative to the maximum of the diffraction-limited point spread function for a given pupil size, or the volume of the modulation transfer function relative to the volume under the diffraction-limited modulation transfer function for a given pupil size. The strehl ratio, generally, may evidence a diffraction-limited system if the ratio is greater than about 0.8, which represents the Rayleigh criterion. For example, the image quality may be measured using the modulation transfer function and have any value in the range of 0.01-1.0, or 1%-100%.

Emmetropia describes the state of vision wherein an object at infinity is in sharp focus, i.e., has high image quality in accordance with the defocus curve, with the eye in a relaxed state. For an emmetropic eye, the eye has an optimum focus when spectacle lens 20 has a power of zero diopters. For the exemplary emmetropic eye, a negative spectacle lens power mimics the effect of looking at an object at a close distance, and a positive spectacle lens power mimics an object beyond infinite distance.

FIG. 2 depicts an eye 100 having corneal astigmatism. FIG. 2 includes a cornea 110 having a first curvature 120 on a first meridian, and a second curvature 130 on a second meridian that is typically, although not necessarily, perpendicular to the first meridian. Although FIG. 2 depicts one meridian vertically and another meridian horizontally, the set of two perpendicular meridians may have any orientation, that is, may be rotated around the optical axis by an angle of "Θ". The variation in curvature along the meridians causes two foci to be imaged by the eye, as discussed hereinabove. The distance between the foci represents the astigmatism.

More specifically, a first focus 140 may be created by first curvature 120 in cornea 110, and a second focus 150 may be created by second curvature 130 in cornea 110. Since the first focus 140 and the second focus 150 are not on the retina, as shown, the foci cannot be on the retina simultaneously using only spherical correction. Consequently, blurry vision results.

As discussed above, a lens may be used to correct for the astigmatism generated within the cornea correspondent to the unique foci of first curvature 120 and second curvature 130. Such a corrective lens may include a toric lens that has a curvature difference between two perpendicular meridians that matches or counteracts the cornea (first curvature 120 and second curvature 130), but that has an oppositely signed (+/−) astigmatism. The opposite astigmatism reduces the total astigmatism in the eye system 10. Just as astigmatism is a measure of the toricity of a lens, as described hereinabove, the negative astigmatism is a measure of a lens having the opposite toricity.

For example, the astigmatism of the cornea may be denoted by an amount, −A, and an orientation "Θ". A proper corrective lens may be selected having an equal and opposite, that is, the negative, astigmatism as compared to the cornea. This equal and opposite value may be denoted as having magnitude +A and orientation "Θ".

If the aforementioned corrective lens were to be implanted in the eye with the corrective magnitude and orientation precisely matching the corneal astigmatic magnitude and orientation, then the corneal astigmatism would be at least substantially reduced, if not cancelled. However, there is typically a small angular error in the orientation of the lens that arises during implantation surgery, δ, so that the astigmatism of the lens is oriented at angle Θ+δ after implantation. This angular error is preferably kept as small as possible, but may not be acceptably limited in practice due to measurement errors when measuring corneal astigmatism, due to measurement errors when measuring corneal astigmatism, misalignments during surgical implantation, postoperative changes in the cornea, postoperative IOL rotation, due to less than ideal surgical procedures, or due to other factors related to the healing of the implanted eye. More specifically, while highly accurate surgical procedures may be able to achieve a δ no greater than about 5 degrees, less ideal surgical procedures or healing processes may result in angular errors larger than 5 degrees, and even an angular error of 5 degrees may result in reduced visual acuity.

The astigmatism of the cornea (amount −A, orientation Θ), plus the astigmatism of the rotationally misaligned lens (amount +A, orientation Θ+δ), results in a residual astigmatism with magnitude 2 A sin δ, oriented at an angle (Θ+δ/2). Additional information regarding residual astigmatism may be found in T. Olsen, "Simple Method To Calculate The Surgically Induced Refractive Change," J Cataract Refract Surg 19(2), 319-320 (1993), the entirety of which is incorporated by reference herein as if set forth in its entirety. For example, an exemplary cornea may have 2 diopters of astigmatism, and a corrective lens may have 2 diopters (of the opposite sign) of astigmatism. If the lens is implanted with an angular error δ of precisely 5 degrees, then the residual astigmatism is (2) (2 diopters) (sin 5°), which is approximately 0.35 diopters. For a tolerance of 10 degrees, the residual astigmatism is (2) (2 diopters) (sin 10°), which is approximately 0.7 diopters. A typical threshold for a visually noticeable astigmatism is 0.25 diopters, meaning that if the light reaching the retina has less than 0.25 diopters of astigmatism, then the astigmatism does not significantly degrade the vision of the eye. As such, the aforementioned angular errors would produce a noticeable astigmatism, and thus may cause patient discomfort and/or sub-optimal post-surgical acuity.

Figure 3:
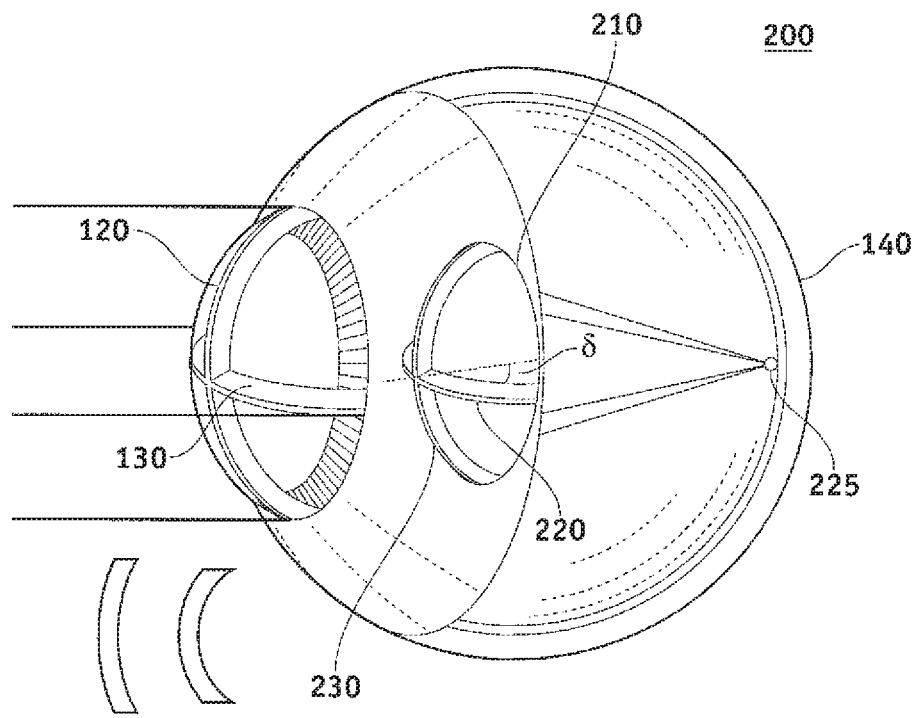
FIG. 3 is a depiction of an eye having corrected astigmatism.

FIG. 3 illustrates an eye 200 having corrected astigmatism. Eye 200 is similar to the astigmatic eye 100 discussed above, with the addition of IOL 210 into eye 100. Eye 100 has astigmatism, as evidenced by the foci depicted on opposite sides of the retina (140 and 150 in FIG. 2). IOL 210 may be toric in design, having a first curvature 220 and a second curvature 230. In order to substantially completely correct, or at least reduce, the astigmatism of eye 100, it is necessary that curvature 220 match or counteract curvature 120, and that curvature 230 matches or counteracts curvature 130, although partial correction may also be achieved by having a substantial curvature match or counteraction in each axis. The corrected astigmatism is shown by focus 225. In addition to matching the curvatures, the correction lens may be aligned with the cornea. Misalignments in the angle of the IOL, either by placement or by post surgical movement, may leave some residual astigmatism as discussed above.

As used herein, the terms "extended focus" or "extended depth of focus" (EDOF) include a depth of focus of a test lens, optic, or optical element that exceeds the depth of focus of a reference optic. The reference optic may have biconvex or biconcave surfaces, which may have equal radii of curvature, and an optical power or focal length that may be equal to an optical power or focal length of the test optic. The depth of focus for the test optic and the reference optic are determined under the same aperture conditions and under equivalent illumination conditions.

In the case wherein the EDOF is attributable to a particular surface feature, structure, or mask associated with the test optic, the reference optic may be made of the same material, and have the same structure, as the test optic, except without the particular feature, structure, or mask. For example, if a test optic is a refractive or diffractive multifocal optic including a mask for extending the depth of focus of at least one of the foci formed by the test optic, then a suitable reference optic may be made of the same material(s) as the test optic and have the same structure as the test optic (e.g., surface shapes/curvatures, thickness, aperture, echelette geometry, and the like), but without the mask.

According to an embodiment, a corrective lens, such as IOL 210, may include the toric lens described above in combination with one or more elements designed to extend the depth of focus. The EDOF element may produce a depth of focus for each meridian. The depth of focus may indicate a good focus for each meridian at a broader range of foci. As used herein, good focus may be a focus that proves useful for vision, and that may be measured using a point spread function, defocus curves, a modulation transfer function (MTF), or by analysis of the Zernike polynomial understood to those skilled in the pertinent arts, for example.

The MTF may be used, for example, to predict or determine good focus, such as by simulation, and/or may be measured of the eye. MTF, therefore, relates to the contrast of alternating bright and dark bars in an image. For example, MTF is 1 when bright bars are completely bright and dark bars are completely dark. MTF is zero when bright bars and dark bars are equally gray. MTF may have a dependence on spatial frequency that is inversely related to the width of the alternating bright and dark bars in an image. Generally, an MTF may be measured using white light or may use green light, such as approximately 550 nm wavelength light, for example, In determining or providing a depth of focus, an extended focus, or an EDOF, the determination may be based on a cut-off of the through-focus MTF at a particular spatial frequency. For example, the depth of focus may be defined as the region in a through-focus MTF over which the MTF, at a spatial frequency of 50 line pairs per mm, exceeds a selected cutoff value. Typical cutoff values may include 0.05, 0.10, 0.15, 0.17, 0.20, 0.25, 0.3, 0.4 or higher. Other spatial frequencies may include 25 line pairs per mm or 100 line pairs per mm, for example.

Further, the depth of focus may be based on a relative threshold, where the threshold is defined based on a peak value of the MTF. Relative thresholds may be 95%, 90%, 80%, 70%, 60%, 50%, 1/e, or $1/e^2$ of a peak value of the MTF, full width at half maximum (FWHM) of the MTF, or any suitable fraction of the peak value of MTF, or of any other metric. For instance, the depth of focus may be defined as the FWHM of the MTF at a particular spatial frequency. As will be understood by a person having ordinary skill in the pertinent arts, FWHM is an expression of the extent of a function, and FWHM is indicated by the difference between two extreme values of an independent variable at the point at which the dependent variable is equal to half of its maximum value.

In certain embodiments, the test optic with an EDOF discussed hereinabove may be evaluated in terms of an MTF, that is, based on optical performance over a range of defocus conditions, as compared to a reference optic, as is also discussed hereinabove. For example, a test optic with an EDOF may have an MTF that is above a predetermined threshold value (e.g., 0.05, 0.10, 0.15, 0.17, 0.20, 0.25, or higher) at a particular frequency (e.g., 25, 50, or 100 line pairs per mm) over a defocus range that is greater than that of the corresponding reference optic. A threshold for acceptable vision may be an MTF at 50 lines per mm greater than 0.2, or preferably greater than 0.4, for example. The defocus range may be expressed in terms of object space distances, image space distances, or diopter power. In certain embodiments, the test optic with EDOF may be specified in terms of an increased depth of focus as compared to the corresponding reference optic, either in absolute terms (e.g., an increased defocus range, compared to the reference optic, over which a predetermined MTF is maintained), or in relative terms (e.g., a percent increase in defocus range, compared to a reference optic, such as a 10%, 20%, 50%, 100%, 200%, or greater increase in defocus range compared to a reference optic).

Alternatively, other psychophysical metrics may be used to evaluate an EDOF element, such as, but not limited to, contrast sensitivity, visual acuity, and perceived blur. In addition, other metrics may be found in the literature, such as those detailed in Marsack, J. D., Thibos, L. N. and Applegate, R. A., 2004, "Metrics of optical quality derived from wave aberrations predict visual performance," J Vis, 4 (4), 322-8; Villegas, E. A., Gonzalez, C., Bourdoncle, B., Bonnin, T. and Artal, P., 2002, "Correlation between optical and psychophysical parameters as a function of defocus," Optom Vis Sci, 79 (1), 60-7; van Meeteren, A., "Calculations on the optical transfer function of the human eye for white light," Optica Acta, 21 (5), 395-412 (1974). Each of the immediately foregoing references is herein incorporated by reference in the entirety.

As indicated by an MTF, for example, a retinal image may not suffer from astigmatism from any residual uncorrected power as a result of cornea and toric IOL mismatch, if the uncorrected power is smaller than the depth of focus provided by the EDOF element of the IOL. Similarly, the retinal image will not suffer from astigmatism when rotation of the IOL introduces an astigmatism that is smaller than the depth of focus provided by the EDOF element of the IOL. The EDOF element may preferably be independent of rotation by having a rotational symmetry in order to minimize rotational effects during implantation or in-vivo, for example. Conversely, the EDOF element may be asymmetric, such as an oval ring shape, correspondent to, for example, asymmetric aspects of a subject eye, such as a pupil size or shape, for example.

For example, the EDOF element may take the form of a low power diffractive element having a single diffractive structure. In such a configuration, the toric structure may be placed on the anterior surface of the IOL, and the diffractive structure may be placed on the posterior surface.

The EDOF element may also take the form of any element that increases the depth of focus. The EDOF element may be used in conjunction with a bifocal lens or a trifocal lens. If the IOL is an EDOF element only, as discussed below with respect to FIG. 8, a bifocal lens may add to the power of the cylinder.

A plurality of echellettes, including a central echellette, may serve as an EDOF element in accordance with certain disclosed embodiments, and as described with respect to U.S. patent application Ser. No. 12/120,201, which is hereby incorporated by reference as if set forth herein in its entirety. Additional EDOF elements are also illustratively provided in U.S. patent application Ser. No. 12/197,249, which is also incorporated by reference as if set forth herein in its entirety.

A toric EDOF, as discussed further hereinbelow with respect to FIGS. 4-5 and 7-8, may be combined with another diffractive element that may be designed to improve retinal image quality. The toric lens associated with such an EDOF element may be aspheric, and/or diffractive, and/or any type of toric design indicated to those skilled in the pertinent arts in light of the discussion herein. The EDOF element may include any element, item or method, or combinations thereof, for extending the depth of focus. The proposed lens may be combined with a monofocal IOL, multifocal IOL, and/or accommodating IOL, by way of non-limiting example only. More specifically, an EDOF element as described herein may be added to a toric element, such as aspheric, multi-focal, or accommodating IOL, for example, in order to provide the benefits described herein.

Referring now to FIG. 4, there is shown the anterior surface 310 of a lens, such as IOL 210, according to an embodiment. Anterior surface 310 may include a toric structure 330. As may be seen in FIG. 4, toric structure 330 includes a first curvature 340 and a second curvature 350. For example, first curvature 340 may be along a first meridian and oriented vertically, and second curvature 350 may be along a second meridian and oriented horizontally.

With reference to FIG. 5, there is shown the posterior surface 410 of a lens, such as IOL 210, according to an embodiment. Posterior surface 410 includes an EDOF element 430. EDOF element 430 may include a low power diffractive element having a single diffractive structure 440. Single diffractive structure 440 may include an annular structure that may be designed to provide the extended depth of focus. Examples of a single diffraction structure include an annulus, zonal monofocal, low add refractive bull's-eye and/or a ring structure having a periodicity and/or structure to manipulate focus. These and additional single diffraction structures for use in embodiments may be modeled using known optical modeling techniques, including Zemax, Code V, and other software, and the Liou-Brennan model for the human eye, in conjunction with the model eye of FIGS. 1A and B, to determine defocus curves, and to provide diffractive structures that operate to increase the depth of focus.

According to another embodiment, and by way of non-limiting example only, toric structure 330 may have 4 diopters of cylinder. EDOF element 430 may be a single diffractive structure that represents an add power of 1.33 diopter, corresponding to about 1 diopter in the spectacle plane, for example.

Figure 6:
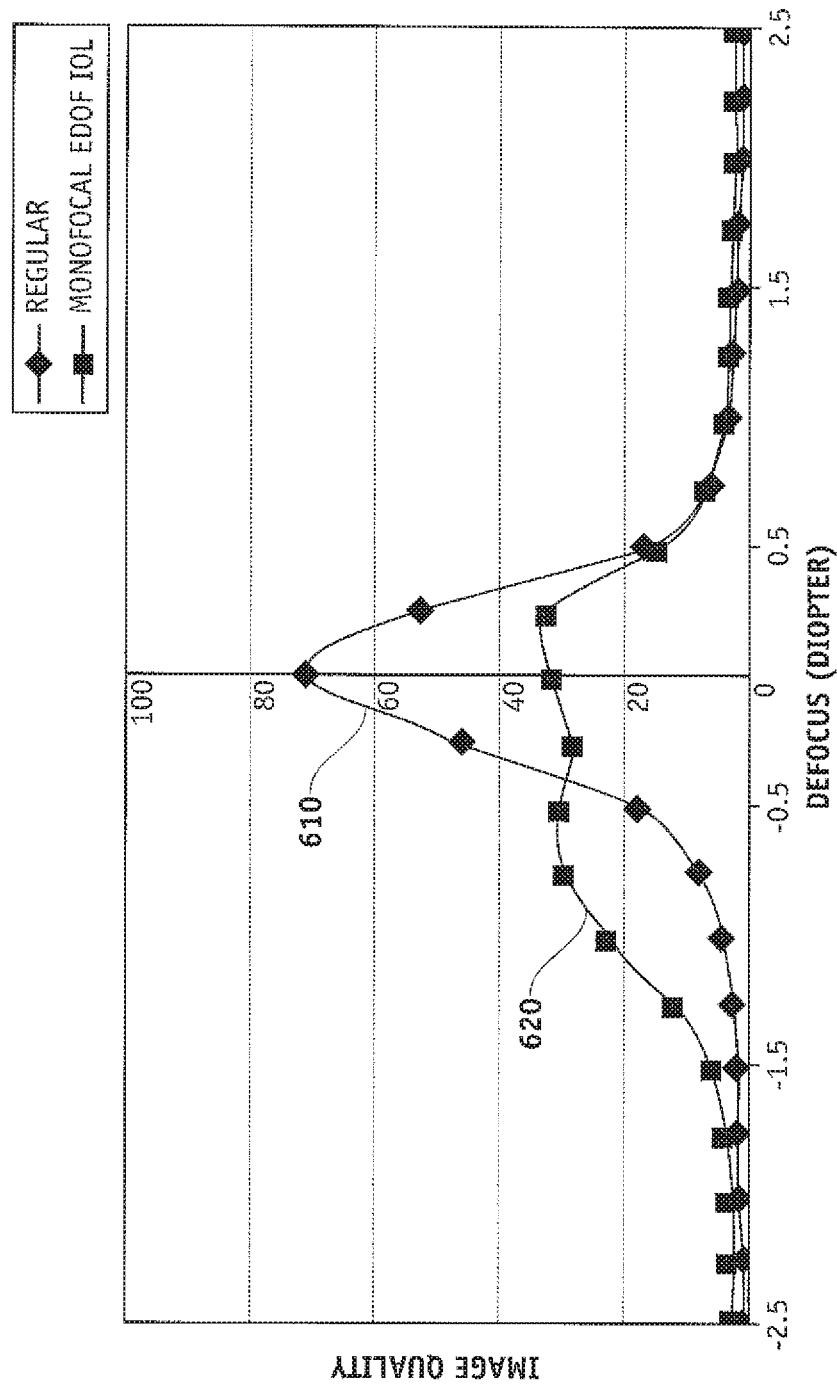
FIG. 6 is a plot of image quality with respect to defocus for a pseudophakic eye having no astigmatism.

Referring now to FIG. 6, there is shown a plot of image quality, as defined hereinabove, with respect to defocus for a pseudophakic eye having no astigmatism. The plot of FIG. 6 is generated with respect to the schematic eye of FIGS. 1A and B. As would be understood by those possessing an ordinary skill in the pertinent arts, a pseudophakic eye is an eye that has an IOL implant present, and that has the crystalline lens of the eye removed. In the first case (diamond plot 610) of FIG. 6, the eye has a regular monofocal lens implanted, and, in the second case (square plot 620), the eye has a monofocal EDOF IOL implant having an extended depth of focus. The curves of FIG. 6 illustrate the trade-off between maximum image quality achievable for a prior art monofocal IOL, and the decreased, but broader range of acceptable image quality available due to the increased depth of focus of the EDOF IOL plotted as an acceptable image quality over a range of defocus greater than 0.2 or 0.1, for example.

As illustrated in FIG. 6, a monofocal IOL in accordance with the prior art may provide an image quality maximum of about 70, with a FWHM of less than 1 diopter of defocus. An EDOF IOL may provide an image quality of approximately 35, with a FWHM of approximately 2 diopters of defocus. Further, at an image quality maximum of approximately 15-20, for example, the prior art IOL has a depth of focus of approximately 1 diopter, while the EDOF IOL of the present invention has a depth of focus of approximately 2 diopters.

Thus, although the ideal image quality achieved with the prior art IOL may be higher at maximum than the EDOF IOL, this peak image quality is seldom achieved using the prior art IOL because of postoperative ametropia (defocus), alignment problems, or due to healing, and/or because of cylinder power selection problems. Simply put, the plot of FIG. 6 illustrates that the EDOF IOL of the present invention consistently provides a patient with a highly acceptable image quality after implantation, unaffected by the prior art need for ideal circumstances, due in part to the greatly increased range over which an acceptable image quality is provided by the EDOF IOL.

Figure 7:
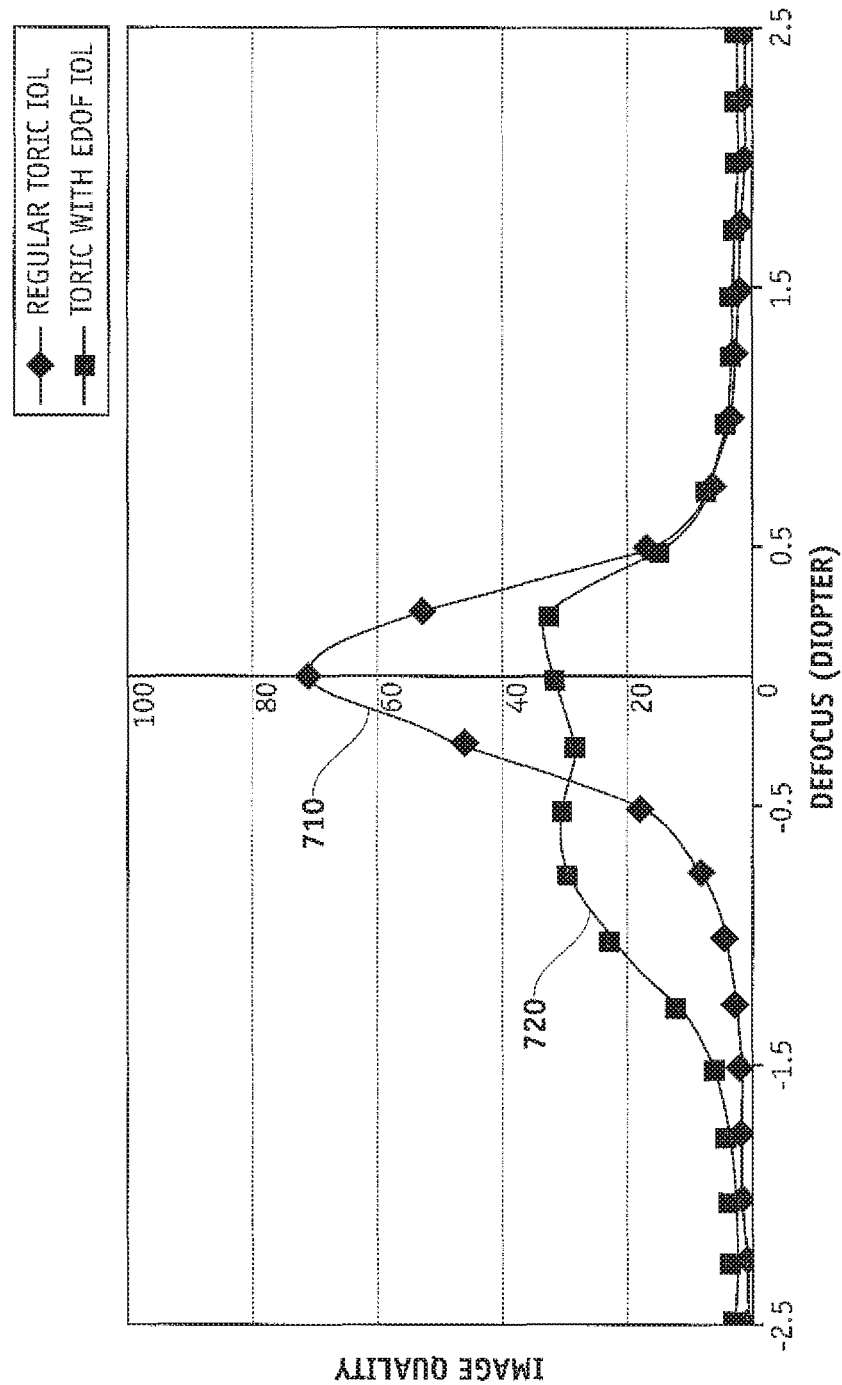
FIG. 7 is a plot of image quality with respect to defocus for an eye in which the cornea has astigmatism.

Referring now to FIG. 7, there is shown a plot of image quality with respect to defocus for an eye in which the cornea has astigmatism, as discussed hereinabove. As explained previously, when the eye has astigmatism, the astigmatism may be corrected by a toric lens. This correction may be ideal when the amount of cylinder power and the cylinder axis match that of the cornea in a pseudophakic eye to thereby cancel any astigmatism, such a circumstance will produce the curves of image quality plotted against defocus shown in FIG. 6 for both meridians. If the cylinder power and axis are not matched, then the eye will be left with a residual amount of cylinder, i.e. astigmatism.

FIG. 7 shows the situation in which the cornea has no or neglible residual cylinder. In one case (diamond plot 710), the eye has an essentially perfectly matched prior art toric IOL implanted, and, in the other case (square plot 720), the eye has a toric EDOF IOL implanted having an extended depth of focus. The plot demonstrates the tradeoff between maximum image quality achieved over a narrow range for the prior art toric IOL, and the improved image quality over a much broader range provided by the toric EDOF IOL.

Figure 8:
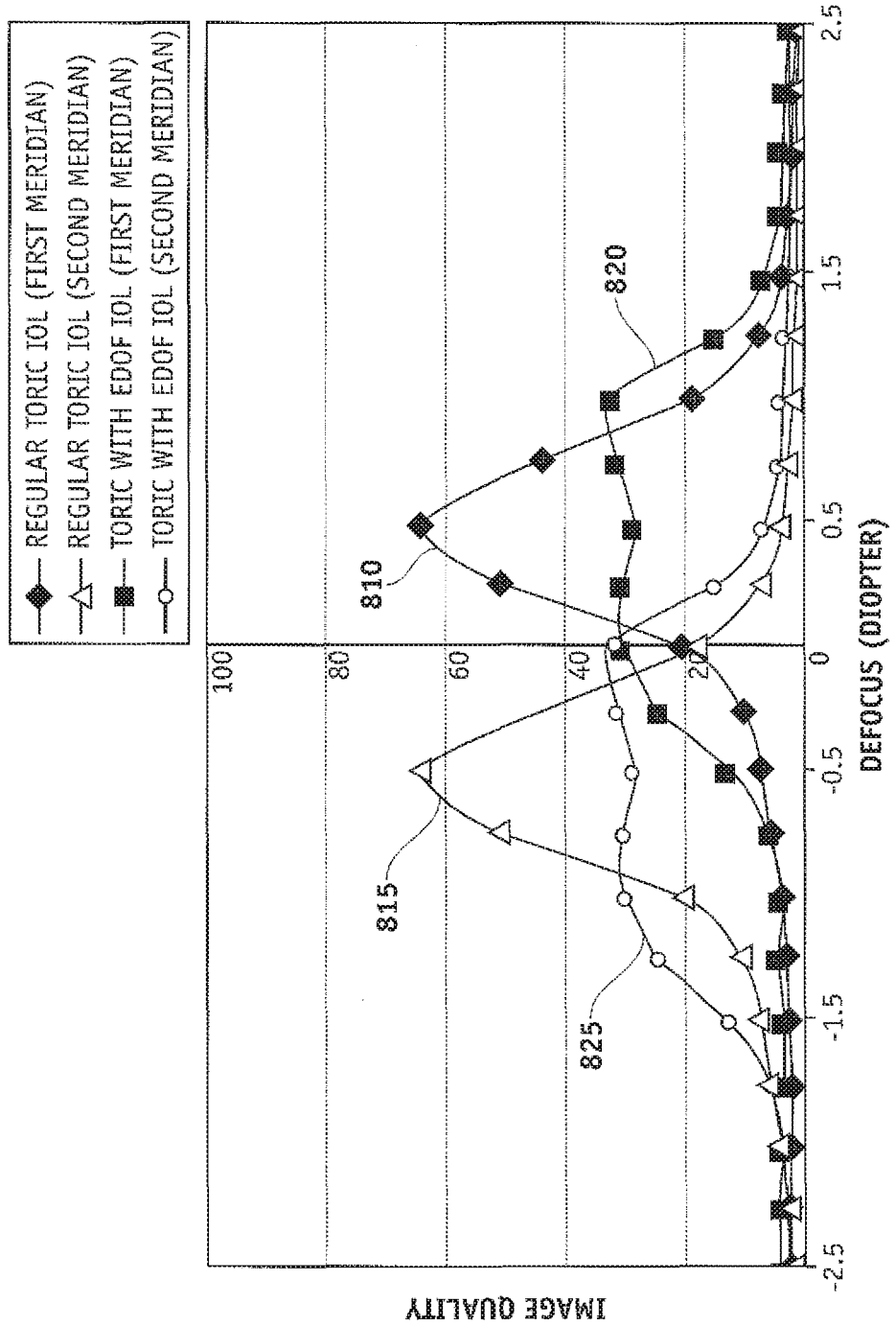
FIG. 8 is a plot of image quality along the meridians of highest and lowest optical power, with respect to defocus of an astigmatic eye correction having 1 diopter of residual cylinder resultant from alignment and cylinder power selection errors.

Referring now to FIG. 8, there is shown a plot of image quality with respect to defocus of a correction in which there is about 1 diopter of residual cylinder that may result from either an alignment error, a mismatch between cylinder power of the cornea and the IOL, or both. Because an eye having a residual amount of cylinder, or astigmatism, has a different image quality in each meridian, the defocus curves also differ for each meridian. That is, the defocus curve may reflect that the difference between the minimum power and the maximum power is equal to the residual cylinder. The plot of FIG. 8 shows two defocus curves for each situation, one in which the meridian has a maximum power, and one in which the meridian has a minimum power.

FIG. 8 further illustrates the presence of residual cylinder. In one case, with first meridian (diamond plot 810) and second meridian (triangle plot 815), the eye has a prior art toric IOL implanted, and, in the other case, with first meridian (square plot 820) and second meridian (circle plot 825), the eye has a toric EDOF IOL implanted. In both cases, the defocus curves are shown for the meridians of highest and lowest optical power. FIG. 8 demonstrates that, for both cases, the image quality at each meridian may be about the same at approximately zero defocus. This may occur because the respective maximum optical power and respective minimum optical power of each defocus curve is about equally displaced from zero defocus. FIG. 8 also demonstrates that the image quality may be higher for the implanted lens with the EDOF implanted than for an implantation of the prior art toric IOL alone.

More specifically and by way of specific example, for an eye having a prior art toric IOL without an EDOF element, with about 1 diopter of residual cylinder, the best focus for an image may be at a zero defocus, whereat an image quality of about 20 may be achieved. In contrast, for an eye having a toric IOL including an EDOF element, and with about 1 diopter of residual cylinder, the best focus for the image may be at zero defocus, whereat an image quality of about 30 may be achieved. Thus, the toric IOL with the EDOF may achieve an increased image quality when surgical, selection, implantation, or environmental errors occur, such as an error in the form of 1 diopter of residual cylinder, as compared to the prior art toric IOL. More specifically, by use of an EDOF element that broadens and flattens the curve for a range of acceptable image quality over a range of defocus, an EDOF IOL may improve the image quality equal to or greater than about 50%.

For example, it has been experimentally assessed that a lens, such as an IOL, incorporating an EDOF element may optimally produce a retinal image with reduced residual astigmatism, and thus with increased image quality, when the eye astigmatism is between about 0.5 and 10 diopter, and more specifically between about 0.5 and 6 diopters, and yet more specifically between about 0.5 to 5 diopters. This assumes no appreciable measurement errors for astigmatism, essentially perfect control over surgically induced astigmatism, and essentially perfect alignment of the lens. As mentioned previously, lens alignment errors (such as rotation) may result in an increase of residual astigmatism, and a change of the cylinder axis. Nonetheless, within these limits, the proposed lens, such as an IOL, may produce a retinal image without appreciable astigmatism, as long as the residual astigmatism is smaller than the depth of focus, such as about 1 or 2 diopters, of the EDOF element.

According to an embodiment, when the corrected astigmatism is small, such as in the range of about 0 to 3 diopters, or more specifically in the range of about 0 to 2 diopters, or yet more specifically in the range of about 0 to 1 diopters, the proposed lens may be used with essentially zero cylinder, that is, may be used with respect to only the EDOF aspects described herein. This is a significant advantage, in part because the axis of small amounts of astigmatism are difficult to measure, and therefore are not only difficult to correct, but are also easily worsened. Use of embodiments with zero cylinder may provide for an avoidance of any worsening of a minor, immeasurable prior condition. Further, the proposed lens using only the EDOF element may work independent of the axis, thereby further alleviating the alignment issues in the prior art.

Figure 9:
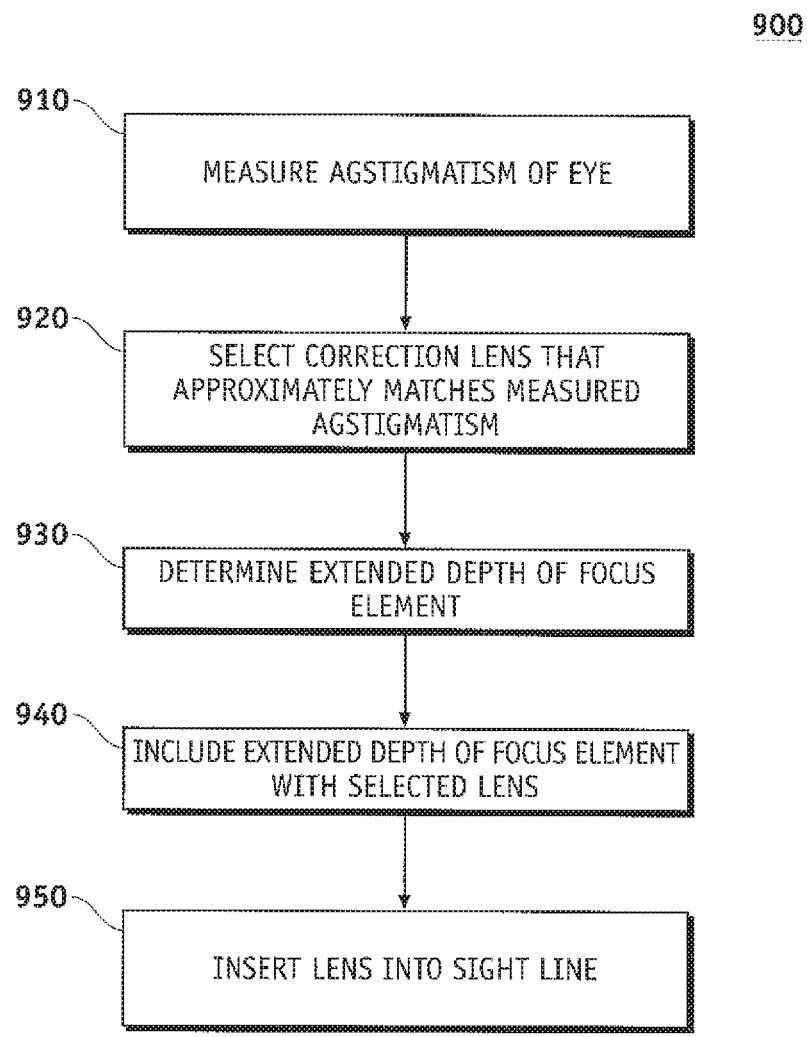
FIG. 9 is a flow diagram illustrating a method for decreasing the sensitivity of astigmatic correction to errors of cylinder power selection and rotational alignment.

Referring now to FIG. 9, there is shown a method 900 for decreasing the sensitivity of astigmatic correction to errors of cylinder power selection and rotational alignment. Method 900 includes receiving (and/or generating) a measured astigmatism of the eye 910. Method 900 may further include receiving (and/or providing) a selection of toric lens 920 that most closely matches or counteracts the measured astigmatism. An EDOF element determination may be received (and/or provided) 930 for use in increasing the depth of focus of the selected lens. The determined EDOF element may be received (and/or provided) 940 in combination with the selected toric lens. The combined toric lens and the EDOF element may be used to correct 950 the measured astigmatism, providing a decreased sensitivity to astigmatic correction errors of cylinder power selection and rotational alignment.

The determination of the EDOF element, such as step 930, may be performed based upon historic data of residual astigmatism. For example, the historic residual astigmatism as obtained with a prior art toric IOL may be used as the defocus range for the EDOF element. For further enhancement, the historic data may be broken down by surgical procedure, by cylinder power, by patient group, by surgeon, and by combinations of these sources, for example. By way of non-limiting example, history may show that, for a desired tolerance with a 5-10 degree misalignment on average, and with 1-2 diopters of residual astigmatism, an EDOF element with 1-2 diopters of EDOF is optional. Alternatively, the EDOF element may be chosen equal or proportional to $2A \sin 2\delta$, in which A is the corneal astigmatism, and $\delta$ is the maximum predicted misalignment.

It should be appreciated in light of the disclosure herein that the method of the present invention may also be applied as a laser refractive procedure, and/or may be applied on an adjustable ophthalmic lens. It should be further appreciated that the method may be applied as a custom lens design, and or as a combined procedure, such as by combining a diffractive EDOF element IOL with a toric laser refractive procedure, for example.

In an illustrative embodiment, and as discussed herein at least with respect to FIGS. 2-5 and 8-9, the cornea may have astigmatism. The horizontal meridian may be the low power meridian, and may have a corneal power of 40 diopters. The vertical meridian may be the high power meridian, and may have a corneal power of 43 diopters. As such, the corneal astigmatism may be 3 diopters, with an orientation of zero degrees. A toric IOL that matches or counteracts the corneal astigmatism, such as with low meridian along the vertical and high meridian along the horizontal, may have astigmatism of approximately 4 diopters, as a result of the fact that the IOL is located within the eye, as opposed to a contact lens, for example, which may be chosen to correct the astigmatism of this example by precisely matching the astigmatism of 3 diopters.

In this example, the clinical history of the surgeon, using a conventional toric IOL, may indicate an average residual astigmatism of about 0.3 diopters. This residual astigmatism may result from the combined errors of cylinder mismatch, IOL rotation, surgically induced astigmatism, and the like. An EDOF element may thus be selected having a depth of focus of at least 0.3 diopters. For example, the EDOF element may produce a depth of focus of 0.75 diopters in the corneal plane, and thus about 1 diopter in the IOL plane.

By way of additional example, kits or quasi-custom designs may be utilized. For example, knowing the trade-offs between misalignment tolerance and MTF limits, a surgeon may desire up to 10 degrees of misalignment tolerance and a MTF greater than 0.2, and may consequently select a Type 1 lens and EDOF element. If the surgeon desires 5 degrees of misalignment tolerance and an MTF greater than 0.3, a selection of a Type 2 lens and EDOF element may be indicated.

An EDOF element may be achieved by using any number of EDOF elements. For example, the provided EDOF element may be a low power diffractive bifocal structure on the posterior surface of the IOL. The diffractive bifocal structure may have multiple rings, or may be selected with a central diffractive echellette having a diameter of 2 mm, for example. The resulting lens may have a toric anterior surface, with astigmatism of 4 diopters, and on the posterior surface may have a diffractive element producing a depth of focus of 1 diopter. Such an IOL may tolerate a mismatch between the cornea and IOL of +/−0.5 diopter, and a total range of 1 diopter, in the IOL plane. The lens may tolerate a rotation of about 5 degrees, and thus rotation of greater than 5 degrees may produce a residual astigmatism that is approximately 0.5 diopters lower than a similar configuration using a conventional toric IOL.

Although the invention has been described and pictured in an exemplary form with a certain degree of particularity, it should be understood that the present disclosure of the exemplary form has been made by way of example, and that numerous changes in the details of construction and combination and arrangement of parts and steps may be made without departing from the spirit and scope of the invention as set forth in the claims hereinafter.

The invention claimed is:

1. An intraocular lens, comprising: an optic comprising a first surface having a first shape and an opposing second surface having a second shape, the first and second shapes providing a refractive power; a diffractive pattern imposed on at least one of the first shape and the second shape; the first and second surfaces providing a base power and an add power; wherein, when the optic is placed in an intraocular lens plane of a physical eye model including a model cornea, the modulation transfer function of the eye model exceeds about 0.17, at a spatial frequency of about 50 line pairs per millimeter, over a range of at least about 1.7 Diopters.

2. An intraocular lens, comprising: a first surface having a first shape and an opposing second surface having a second shape, the first and second shapes providing a refractive power; a diffractive pattern imposed on the first shape or the second shape; the first and second surfaces providing a base power and an add power; the intraocular lens having a depth of focus, when illuminated by a light source, that is at least about 30% greater than that of an intraocular reference lens without the diffractive pattern, the intraocular reference lens having a refractive power that is equal to the base power of the intraocular lens.

3. The intraocular lens of claim 2, wherein the light source is a polychromatic light source.

4. The intraocular lens of claim 2, wherein the light source is at a predetermined wavelength and the intraocular lens has a depth of focus, when illuminated at the predetermined wavelength, that is at least about 50% greater than that of the intraocular reference lens.

5. The intraocular lens of claim 2, wherein, at a spatial frequency of about 50 line pairs per millimeter, the modulation transfer function of the lens exceeds 0.17 over a depth of focus that is greater than the depth of focus for the reference intraocular lens by at least about 0.5 Diopters.

6. The intraocular lens of claim 2, wherein the intraocular lens is optically described by a model lens, such that when the model lens is included in an intraocular lens plane of an eye model including a model cornea, the modulation transfer function of the eye model exceeds about 0.17, at a spatial frequency of about 50 line pairs per millimeter, over a range of at least about 1.7 Diopters.

* * * * *